United States Patent
Zheng et al.

(10) Patent No.: US 8,444,645 B2
(45) Date of Patent: May 21, 2013

(54) METHOD AND DEVICE FOR COMPUTER ASSISTED DISTAL LOCKING OF INTRAMEDULLARY NAILS

(75) Inventors: Guoyan Zheng, Bern (CH); Xuan Zhang, Bern (CH)

(73) Assignee: AO Technology AG, Chur (CH)

( * ) Notice: Subject to any disclaimer, the term of this patent is extended or adjusted under 35 U.S.C. 154(b) by 1050 days.

(21) Appl. No.: 12/090,261

(22) PCT Filed: Aug. 15, 2006

(86) PCT No.: PCT/CH2006/000432
§ 371 (c)(1),
(2), (4) Date: Apr. 15, 2008

(87) PCT Pub. No.: WO2008/019510
PCT Pub. Date: Feb. 21, 2008

(65) Prior Publication Data
US 2008/0281334 A1    Nov. 13, 2008

(51) Int. Cl.
*A61B 17/56* (2006.01)
(52) U.S. Cl.
USPC .................................. 606/64; 606/97; 606/98
(58) Field of Classification Search
USPC ...... 606/62–68, 97–99, 102, 95, 96; 600/426, 600/429, 407; 248/222.41, 223.21; 411/383, 411/384, 418, 419
See application file for complete search history.

(56) References Cited

U.S. PATENT DOCUMENTS

| | | | |
|---|---|---|---|
| 5,584,838 A * | 12/1996 | Rona et al. | 606/96 |
| 6,503,249 B1 * | 1/2003 | Krause | 606/62 |
| 6,856,827 B2 * | 2/2005 | Seeley et al. | 600/426 |
| 6,917,827 B2 * | 7/2005 | Kienzle, III | 600/427 |
| 2003/0004518 A1 * | 1/2003 | Perren et al. | 606/102 |
| 2004/0111024 A1 * | 6/2004 | Zheng et al. | 600/426 |
| 2004/0143340 A1 * | 7/2004 | Tuma et al. | 623/22.12 |
| 2004/0181149 A1 * | 9/2004 | Langlotz et al. | 600/431 |
| 2005/0027304 A1 | 2/2005 | Leloup et al. | |
| 2005/0080427 A1 * | 4/2005 | Govari et al. | 606/98 |

(Continued)

FOREIGN PATENT DOCUMENTS

| | | |
|---|---|---|
| WO | 03/043485 | 5/2003 |
| WO | 2005/000129 | 1/2005 |

OTHER PUBLICATIONS

Yaniv, Z. et al.; "Precise robot-assisted guide positioning for distal locking of intramedullary nails;" Database Inspec (online); The Institution of Electrical Engineers; Stevenage, Great Britain; May 2005; XP002433206.

*Primary Examiner* — Ellen C Hammond
*Assistant Examiner* — Atiya Mahmud
(74) *Attorney, Agent, or Firm* — Rankin, Hill & Clark LLP (57) ABSTRACT

A method for computer assisted localization of the distal locking holes (11; 14) of an implanted intramedullary nail (2) having a nail axis (19) and a first and second distal locking hole (11; 14) by A) acquiring one single image IM of the distal end section (25) of said intramedullary nail by means of an X-ray device (9) whose optical axis (30) is oriented essentially perpendicular to the nail axis (19) but irrespective to the orientation of the distal locking holes (11; 14); and B) calculating the position of the first and second hole axis (23; 20) of the first and second distal locking hole (11; 14) with respect to a three-dimensional coordinate system A-COS (7) of the implanted intramedullary nail (2).

9 Claims, 5 Drawing Sheets

U.S. PATENT DOCUMENTS

| | | | |
|---|---|---|---|
| 2005/0203539 A1* | 9/2005 | Grimm et al. | 606/99 |
| 2005/0261700 A1* | 11/2005 | Tuma et al. | 606/96 |
| 2006/0064106 A1* | 3/2006 | Fernandez | 606/98 |
| 2006/0122495 A1* | 6/2006 | Kienzle, III | 600/424 |
| 2006/0173293 A1* | 8/2006 | Marquart et al. | 600/426 |

* cited by examiner

METHOD AND DEVICE FOR COMPUTER ASSISTED DISTAL LOCKING OF INTRAMEDULLARY NAILS

BACKGROUND OF INVENTION

1. Field of Invention

The invention relates to a method for computer assisted localization of the distal locking holes of an implanted intramedullary nail and to a device for the computer assisted distal locking of an intramedullary nail.

2. Description of Related Art

It is known that one of the most difficult steps of intramedullary nailing of e.g. femoral shaft fractures is distal locking—the insertion of distal interlocking screws, for which it is necessary to know the positions of the distal locking holes (denoted in the following as DLHs) of the intramedullary nail (IMN). The process of locating and inserting the distal interlocking screws is complicated by the nail deformation during insertion. It is known that deformation occurs in several planes due to medio-lateral (ML) and antero-posterior (AP) flexion of the intramedullary nail during its insertion. The reason for the wide variations of the insertion-related intramedullary nail deformation is due to the fact that the nail has to deform to the shape of the medullary canal upon insertion. The shape of the canal varies widely from person to person. It is not possible to predict how the nail will deform accordingly. In a conventional surgical procedure the surgeon depends on intra-operative X-ray means for providing precise positions of the DLH's. It requires positioning the axis of the fluoroscope coaxial to the locking holes so that these holes appear perfectly circular in the images. This is achieved through a trial-and-error method and requires long time X-ray exposure for both the surgeon and patient. It has been reported that the surgeon's direct exposure to radiation for each conventional surgical procedure was 3-30 min, of which 31%-51% was used for distal locking.

The object to target accurately the DLHs with as little as possible X-ray exposure has led to various attempts to develop image-based methods for recovering the positions of the DLHs.

A computer assisted intramedullary rod surgery system is known from WO 03/043485 KIENZLE. In order to determine the position of the nail axis and of the distal locking holes of the intramedullary nail two fluoroscopic images are to be acquired, one in an approximate antero-posterior direction of the bone and a second in a lateral-medial direction of the bone. Subsequently, image processing algorithms are used to calculate the position of the nail axis as well as of the distal locking holes. This known method shows the drawback that the acquisition of the mentioned two fluoroscopic images requires a repeated and cumbersome displacing and rearranging of other surgical apparatus, devices and instruments in order to rotate e.g. the C-arm of the X-ray device from the antero-posterior direction to the lateral-medial direction.

Further, a method for robot-assisted guide positioning for distal locking of intramedullary nails is disclosed in: Ziv Yaniv, Leo Joskowicz, IEEE TRANSACTIONS ON MEDICAL IMAGING, Vol. 24, No. 5 May 2005. This known method requires only one fluoroscopic image, but in a view exactly parallel to the axes of the distal locking holes, such that the distal locking holes appear as circles (and not as ellipses) in the image. In order to correctly adjust the fluoroscope an X-ray technician must use a try-and-move method several times to achieve the correct adjustment of the C-arm of the X-ray device which typically requires 2-6 images to be taken with the X-ray device. The requirement of a fluoroscopic image in a view exactly parallel to the axes of the distal locking holes therefore shows the drawback of a very time-consuming adjustment procedure of the fluoroscope.

On this point the invention intends to provide remedial measures. The invention is based on the objective of providing a method for solving the above problems using one single calibrated fluoroscopic image taken in a lateral-medial direction of the bone only independent of the orientation of the distal locking holes.

BRIEF SUMMARY OF THE INVENTION

The invention solves the posed problem with a method for computer assisted localization of the distal locking holes of an implanted intramedullary nail and with a device for the computer assisted distal locking of an intramedullary nail.

One of the advantages of the present invention is due to the acquisition of only one single image, which allows to avoid a repeated displacing and rearranging of other surgical apparatus, devices and instruments and which minimizes the X-ray exposure for both the surgeon and the patient.

Another advantage is to be seen in the fact that the positioning of the X-ray device is irrespective to the orientation of the distal locking holes allowing an uncomplicated positioning of the X-ray device.

In a preferred embodiment the method according to the invention comprises the following steps:
  i) entering at least the nail diameter D and the diameter d of the locking holes of the intramedullary nail in the data store of a computer;
  ii) positioning a X-ray device with an optical axis with regard to the distal end section of the intramedullary nail irrespectively to the orientation of the distal locking holes, such that said optical axis is essentially perpendicular to the nail axis;
  iii) acquiring one single image (IM) of the distal end section by means of the X-ray device;
  iv) determining the position of the nail tip, the center of the first distal locking hole and the center of the second distal locking hole on the nail axis in the single image (IM);
  v) calculating the direction of the nail axis in a plane defined through a) the nail tip, b) at least one of the centers of the first and second distal locking holes, and c) the focal point of the X-ray device;
  vi) calculating the position of the first and second hole axis of the first and second distal locking hole with respect to a three-dimensional coordinate system A-COS defined by a dynamic reference base fixedly connected with the intramedullary nail or with a bone in which the intramedullary nail is implanted.

In a further embodiment the single image (IM) of the distal end section of said intramedullary nail is taken by means of the X-ray device in a lateral-medial direction of said intramedullary nail implanted in a bone.

In another embodiment a data set defining a geometrical model of said distal end section is entered in the data store of the computer under step i). This allows the advantage that the geometrical model may comprise distal locking holes with a non-circular, e.g. an oval cross section and/or e.g. a conical distal end section instead of a circular cylindrical distal end section.

In still a further embodiment the calculation under step vi) is performed by an iterative closest projection point algorithm.

In another embodiment the steps iv)-vi) are combined to an iterative calculation procedure.

In yet another embodiment the method further comprises the step of attaching a dynamic reference base at an essentially rigid body formed by the intramedullary nail, a proximal and a distal fragment of a bone.

In a further embodiment the method further comprises the step of measuring the position and orientation of the dynamic reference base with a position measurement device allowing to establish a three-dimensional coordinate system fixedly connected with the intramedullary nail or with a bone in which the intramedullary nail is implanted.

In yet a further embodiment the method further comprises the step of displaying a graphic representation of the first and second distal locking hole including trajectories of the axes of the first and second distal locking hole allowing a surgeon to accurately drill the holes in a bone that are necessary to insert the locking screws in the distal locking holes.

In another embodiment the X-ray device is a C-arm X-ray device.

In still another embodiment the X-ray device is a fluoroscope.

BRIEF DESCRIPTION OF THE DRAWINGS

One embodiment of the invention will be described in the following by way of example and with reference to the accompanying drawings in which.

DETAILED DESCRIPTION OF THE INVENTION

Figure 1:
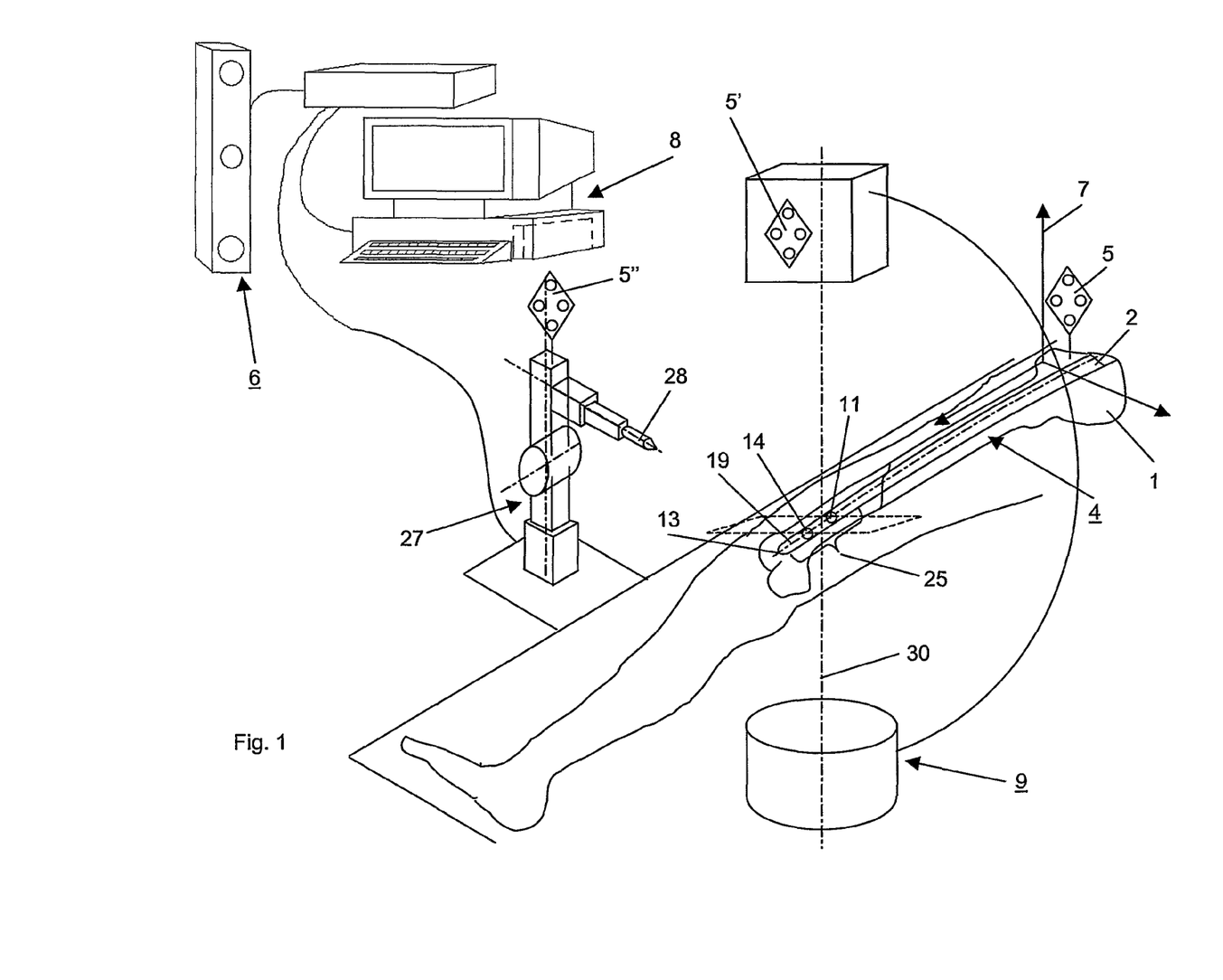
FIG. 1 shows a perspective view of an embodiment of the device according to the invention.

FIG. 1 shows an embodiment of the device according to the invention comprising
  a) a computer 8 having a data store;
  b) a position measurement device 6 for measuring the position and orientation of one or more dynamic reference bases 5;5';5" as known in the field of surgical navigation or computer assisted surgery, whereby said position measurement device 6 is connected to the computer 8;
  c) a dynamic reference base 5 attached at a rigid body 4 formed by an intramedullary nail 2 and the reduced fragments of a fractured bone 1;
  d) a C-arm X-ray device 9 being provided with a dynamic reference base 5',
  e) a roboter 27 being provided with a drill bit 28 and a dynamic reference base 5", such allowing to drill holes necessary for distal locking of an intramedullary nail 2, the position of which has been calculated by means of the computer 8 by referencing the dynamic reference base 5 attached to the rigid body 4, the dynamic reference base 5' at the C-arm X-ray device 9 and the dynamic reference base 5" at the roboter 27 and calculating the position of the axes 23;20 of the distal locking holes 11;14 of the intramedullary nail 2 from a single image IM taken with the X-ray device 9 according to the method as described below. The axis of the drill bit 28 is adjusted subsequently to each of the axes 23;20 of the distal locking holes 11;14 such that the roboter 27 can guide the drill bit 28 under control of the computer 8 in order to drill the holes in a bone 1 that are necessary for the insertion of locking screws in the distal locking holes 11;14.

In the following an embodiment of the method according to the invention is described with reference to FIGS. 1-5:

A) acquiring one single image (IM) of the distal end section 25 of said intramedullary nail by means of an X-ray device 9 whose optical axis 30 is oriented essentially perpendicular to the nail axis 19 but irrespective to the orientation of the distal locking holes 11;14; and B) calculating the position of the first and second hole axis 23;20 of the first and second distal locking hole 11;14 with respect to a three-dimensional coordinate system A-COS 7 of the implanted intramedullary nail 2 as described below:

The proximal fragment of the bone 1, the distal fragment of the bone 1 and the intramedullary nail 2 may be treated as three rigid bodies and registered independently. The rigid transformations between these three rigid bodies are obtained from a navigator or position measurement device 6 such as an optoelectronic tracker, a magnetic tracker, or even a medical robot. According to the present invention it is assumed that the fractured bone 1, e.g. femur has already been reduced and the proximal fragment and distal fragment are kept fixed relative to each other at the time of image acquisition. It is also assumed that the intramedullary nail 2 has been inserted till the distal end of the bone 1, e.g. the bone 1 and has been locked proximally by a bone screw so that the assembly, i.e. the bone 1 and the intramedullary nail 2 can be treated as one rigid body 4. A local coordinate system is established on this rigid body 4 through a common dynamic reference base technique using a dynamic reference base 5. In the following description, this patient coordinate system COS is denoted as a three-dimensional coordinate system 7 (A-COS). All computations effected by the computer 8 are done in this reference A-COS.

To relate a pixel in the two-dimensional (2D) projection image IM acquired by means of an X-ray device 9 to A-COS 7, the acquired image IM has to be calibrated for physical projection properties and be corrected for various types of distortion. A weak-perspective pin-hole camera model may be chosen for modeling the C-arm projection of the X-ray device 9. Using such a camera model, a 2D pixel $V_I$ is related to a three-dimensional (3D) point $V_A$ by following equations:

$$S_A = \frac{(V_A - f_A)}{\|V_A - f_A\|}; \quad (1)$$

and $$\begin{bmatrix} V_{I,x} \\ V_{I,y} \\ 1 \end{bmatrix} = \begin{bmatrix} c_{A,x} & c_{A,y} & c_{A,z} & p_{I,x} \\ r_{A,x} & r_{A,y} & r_{A,z} & p_{I,y} \\ 0 & 0 & 0 & 1 \end{bmatrix} \begin{bmatrix} S_{A,x} \\ S_{A,y} \\ S_{A,z} \\ 1 \end{bmatrix}$$

where $\|\cdot\|$ means to calculate the length of a vector and the vectors $f_A$, $r_A$, $c_A$ and $p_I$ represent the position of focal point 26, the vector along image row increasing direction, the vector along image column increasing direction, and the 2D position of piercing point, respectively. They are projection parameters used to describe the projection properties of the X-ray device 9 and need to be calibrated preoperatively.

Eq. (1) can be used for both forward and backward projections. For example, in order to calculate the direction $s_A$ of the forward projection ray of an image point $V_I$, an additional constraint $\|s_A\|=1$ can be used together with Eq. (1) to solve it. The forward projection ray of point $V_I$ is defined by the focal point 26 and the direction $s_A$.

The position of the imaging plane in the three-dimensional coordinate system 7 (A-COS) and the focal length in our camera model is implicitly determined using the calibrated focal point $f_A$ and the vectors $r_A$ and $c_A$. Any 2D image point $V_I$ corresponds to a 3D spatial point IA in this imaging plane, which is the intersection between its forward projection ray and this plane.

Figure 4:
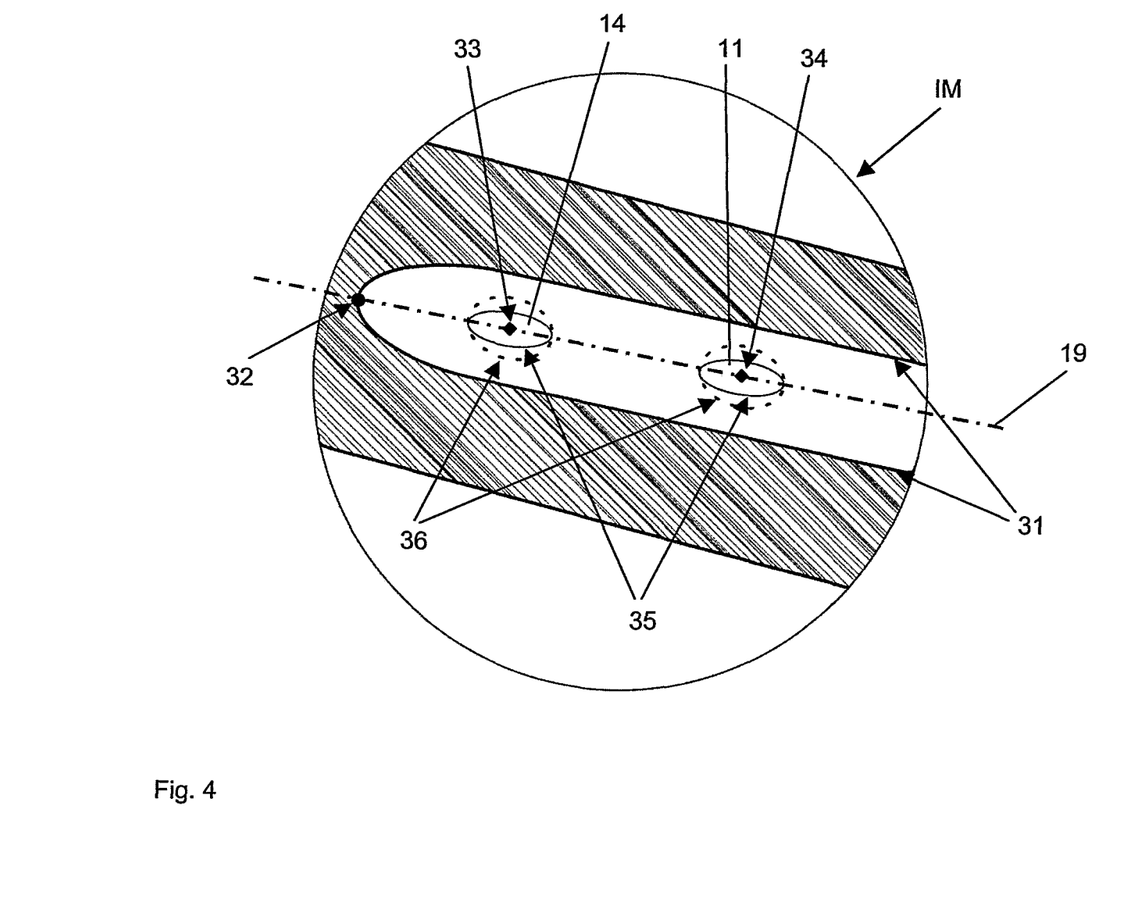
FIG. 4 shows a schematic view of a lateral-medial Image IM of a bone with an inserted intramedullary nail before the "Iterative Closest Projection Point Algorithm" is performed.
Figure 5:
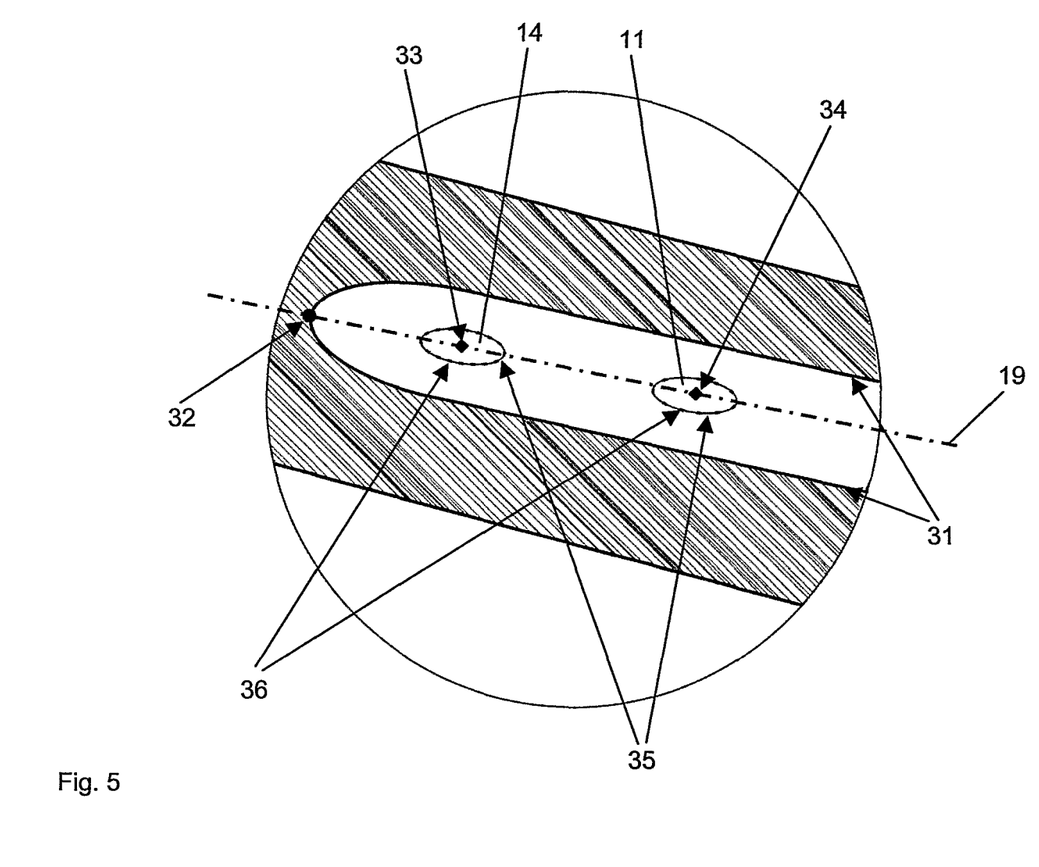
FIG. 5 shows a schematic illustration of the lateral-medial Image IM of FIG. 4 after the "Iterative Closest Projection Point Algorithm" has been performed.

The task of the preprocessing is to determine the projection point 32 of the nail tip 13 and the projection points 33;34 of the centers 21,22 of the distal locking holes 11,14 (FIGS. 4 and 5). To extract these feature points from the image IM (FIGS. 4 and 5), a Hough transform is used to find the two mostly parallel edge lines 31 of the projection of the distal part of the intramedullary nail 2 after applying a Canny edge detector to the image IM. The projection of the nail axis 19 of the distal part of the intramedullary nail 2 is considered as the middle line between these two mostly parallel edge lines 31. To determine those edge pixels belonging to the distal locking holes 11,14, the method reported in Ziv Yaniv, Leo Joskowicz, IEEE TRANSACTIONS ON MEDICAL IMAGING, Vol. 24, No. 5 May 2005 is modified for our purpose. A parallelpiped window, whose sizes are equal to the distance between the detected edge lines, is swept along the middle line to find two locations which contain the maximum number of edge pixels and whose distance is greater than a preselected distance threshold T (e.g. the width of the window). The centroids of the detected edge pixels in both locations are then calculated. The projection point 33;34 of the center 21;22 of each distal locking hole 11;14 is then determined by finding the closest point on the middle line to the associated centroid. The projection point 32 of the nail tip 13 is similarly determined by scanning a cone shaped template along the middle line to find one location that has the highest correlation score.

Figure 3:
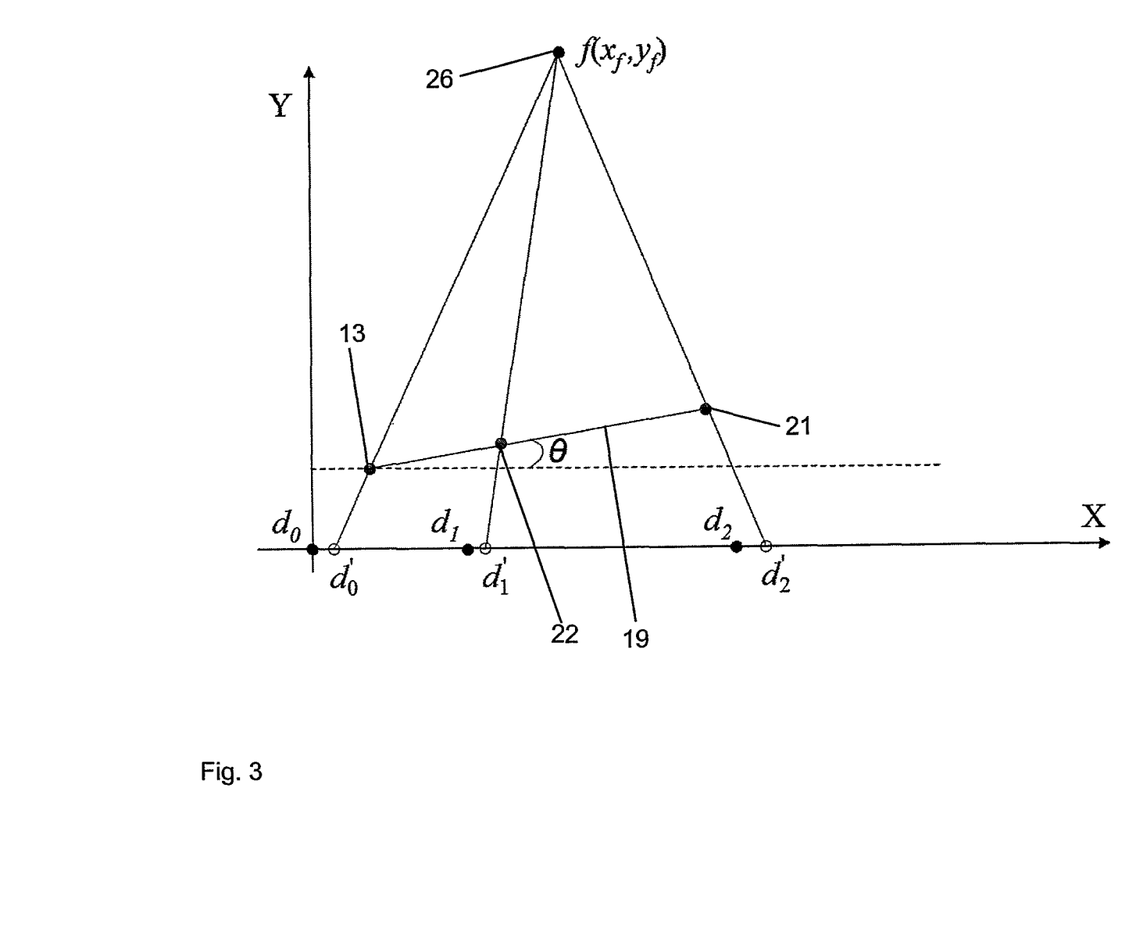
FIG. 3 shows a schematic illustration of an arrangement of the nail axis according to one embodiment of the method according to the invention.

FIG. 3 schematically illustrates the automatic determination of the nail axis 19. Using the above detected feature points, we can find their corresponding spatial points in the imaging plane. Let's denote them as $D^0_A(x^0_A, y^0_A, z^0_A)$ corresponding to the projection point of the nail tip, $D^1_A(x^1_A, y^1_A, z^1_A)$ corresponding to the projection point of the center of the distal DLH, and $D^2_A(x^2_A, y^2_A, z^2_A)$ corresponding to the projection point of the center of the proximal DLH. These three points define a line A-COS. This line together with the focal point $f_A$ defines a plane where the axis of the distal part of the IMN should fall in. Our task now is to determine the exact position of the axis of the distal part of the IMN in this plane. For this purpose, a 2D coordinate system taking DOA as the origin and the line $D^0_A D^1_A D^2_A$ as the X axis is established, as shown by FIG. 3. The coordinates of points DOA, $D^1_A$, $D^2_A$ in this new 2D coordinate system now become $D_0(x_0=d_0=0, y_0=0)$, $D_1(x_1=d_1, y_1=0)$, and $D_2(x_2=d_2, y_2=0)$, respectively. The coordinate of the focal point becomes $f(x_f, y_f)$. The exact position of the axis of the distal part of the IMN in this place can be uniquely determined by a 2D rigid transformation $(\theta, t_x, t_y)$, where $\theta$ is the angle between the axis of the distal part of the IMN and the X axis and $(t_x, t_y)$ defines the translation.

Let's denote the initial position of the three points in the axis, i.e., the nail tip 13, the center 21 of the distal DLH, and the center 22 of the proximal DLH as $N_0(x_0, y_0)$, $N_1(x_1, y_1)$, and $N_2(x_2, y_2)$, respectively. The coordinates of these points can be obtained by assuming that the initial position of this axis is parallel to the X axis and by a rough estimation of the depth of the axis using the ratio between the length of line segment $D^0_A D^2_A$ in the imaging plane and the true length from the center of the proximal DLH to the nail tip. Given a realization of $(\theta, t_x, t_y)$, the transformed coordinates are:

$$\begin{pmatrix} x'_i \\ y'_i \end{pmatrix} = \begin{pmatrix} \cos(\theta) & -\sin(\theta) \\ \sin(\theta) & \cos(\theta) \end{pmatrix} \cdot \begin{pmatrix} x_i \\ y_i \end{pmatrix} + \begin{pmatrix} t_x \\ t_y \end{pmatrix} \quad (2)$$

The projection of these points onto the X axis are:

$$d'_i = \frac{y'_i x_f - x'_i y_f}{y'_i - y_f} \quad (3)$$

The optimal values of $(\theta, t_x, t_y)$ are found by minimizing a joint cost function combining the likelihood energy and the prior energy:

$$\min_{\theta^*, t_x^*, t_y^*} S(\theta, t_x, t_y); \quad (4)$$

where $$S(\theta, t_x, t_y) = \left( \sum_{i=0}^{2} (d'_i - d_i)^2 \right) + \tau \cdot \theta^2$$

where $\tau$ is a parameter that controls the relative weighting between these two terms.

The Iterative Closest Projection Point Algorithm for Pose Recovery of DLHs is schematically illustrated in FIGS. 4 and 5 by means of the simulation 36 of X-ray projections of the distal locking hole models to the image IM and the edges 35 detected from the real X-ray projections of the distal locking holes 11;14 whereby the virtual projections 36 of the distal locking hole models matched to the edges 35 of the real X-ray projections of the distal locking holes together with the known nail diameter D and the diameter d of the distal locking holes allow to establish a geometrical model. FIG. 4 shows the initial state before the Iterative Closest Projection Point Algorithm starts and FIG. 5 shows the final state when the Iterative Closet Projection Point Algorithm converges.

Observing the wide variations of the nail deformation, we are apt for recovering the poses of the two DLHs one by one. In the following descriptions, we concentrate on pose recovery of the distal DLH 14 (FIG. 1). The same principle is applied to the proximal DLH 11 (FIG. 1).

Given the estimated nail axis 19, the initial transformation between the local COS of the geometrical model of the DLH and A-COS can be obtained by taking the estimated nail axis 19 as the u axis and the normal of the imaging place as the v axis of the local COS. All points defined in the local COS of the geometrical model of the DLH can then be transformed to A-COS using this initial transformation. The task of recovery of the DLHs is to resolve the rotation a and the translation δ of the DLH along the axis by fitting the geometrical model of the DLH to the image, which is solved iteratively as follows.

Let's denote E be a set of $N_E$ detected 2D edge pixels $\{e_1, e_2, \ldots, e_{NE}\}$ of the DLH projection. Further denote $M^{t-1}$ be a set of $N_M$ model point $\{m_0^{t-1}, m_1^{t-1}, \ldots m_{Nm}^{t-1}\}$ at iteration step t-1. Now in the iteration step t, we perform following steps:

Simulating X-ray projection: In this step, we simulate the X-ray projection of the geometrical model of the DLH to remove invisible points. Let $p^{t-1}$ be a set of $N_p$ 2D projection points $\{p_1^{t-1}, p_2^{t-1}, \ldots p_{Np}^{t-1}\}$ obtained by simulating X-ray projection of 3D model into the image. Normally $N_p \ll N_M$. Thus, for each 2D projection point $p_t^{t-1}$, we know its associated 3D model point $m_t^{t-1}$.

Find closest projection point: In this step, we try to find the closest neighbor edge pixel $e_t$ of each 2D model projection point $P_t^{t-1}$.

Establishing 3D-2D correspondence: For each 2D matched pairs $(e_t, p_t^{t-1})$, calculate the forward projection ray $BP_t$ of the 2D edge pixel $e_t$. Then for the ray $BP_t$, calculate a 3D point pair $PP_1^{t-1} = (be_t^{t-1}, m_t^{t-1})$, where $be_t^{t-1}$ is a point on the line $BP_1$ that is closest to the 3D model point $m_t^{t-1}$ of the model projection point $p_t^{t-1}$.

Estimating pose: For all calculated 3D point pairs $PPS^{(t-1)} = \{PP_t^{t-1}\}$, find an optimal local solution of all pose parameters by minimizing following cost function:

$$\min_{(\alpha^{(t-1)*}, \delta^{(t-1)*})} \sum_i \|be_i^{t-1} - T(\alpha^{(t-1)}, \delta^{(t-1)}) \cdot m_i^{t-1}\|^2 \quad (5)$$

where $T(\alpha^{(t-1)}, \delta^{(t-1)})$ is a constrained transformation around the axis of the nail determined by rotation angle $\alpha^{(t-1)}$ and translation $\delta^{(t-1)}$.

Updating pose: Update the pose of all model points $\{m_1^{t-1}, m_2^{t-1}, \ldots, m_{Nm}^{t-1}\}$ by $T(\alpha^{(t-1)}, \delta^{(t-1)})$ to $\{m_1^t, m_2^t, \ldots, m_{Nm}^t\}$.

These steps are repeated until all pose parameters are converged.

Figure 2:
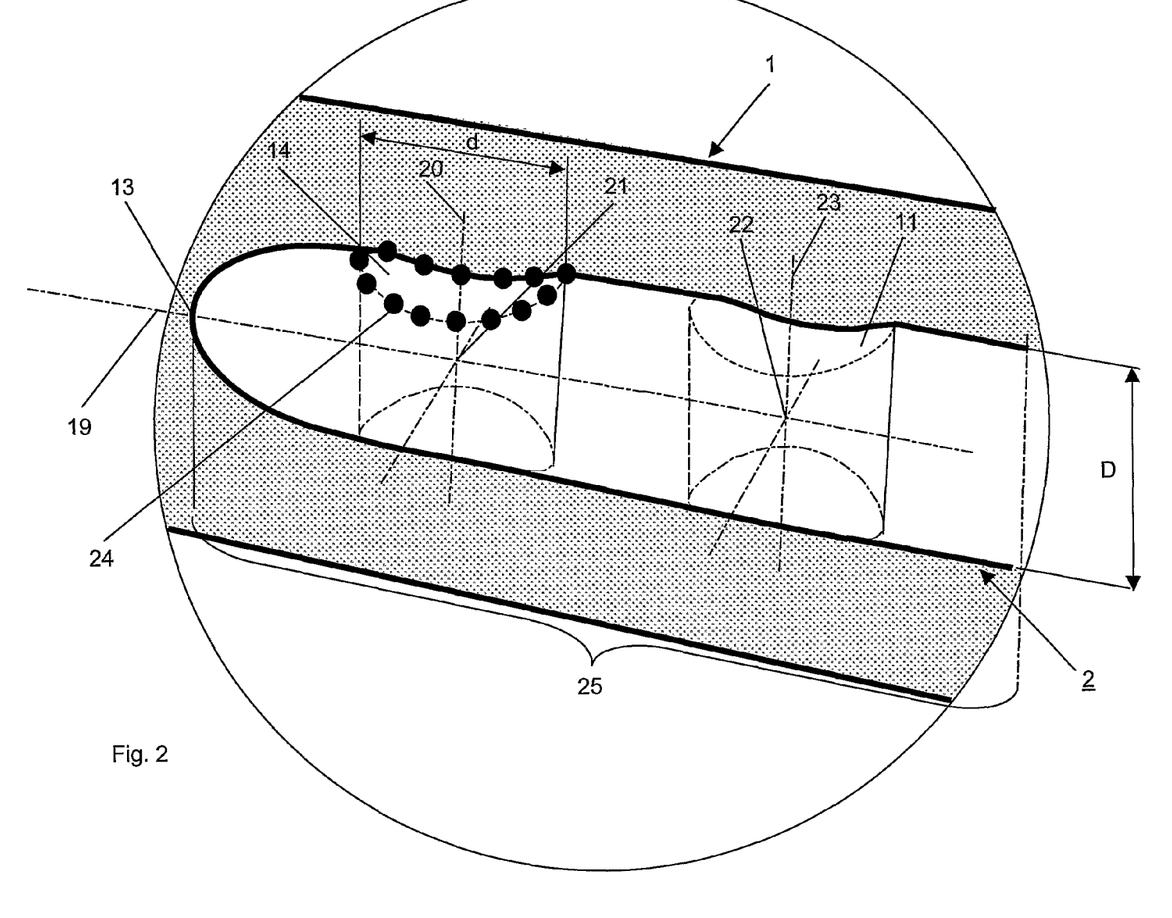
FIG. 2 shows a magnified view of the distal end section of an intramedullary nail to FIG. 1.

In another embodiment the distal end section 25 of the intramedullary nail 2 as illustrated in FIG. 2 is generated as a geometrical model by entering a respective set of data in the data store of the computer 8 in order to display a graphic model at least of the first and second distal locking holes 11;14 e.g. on the display of the computer 8. In order to allow a surgeon to accurately drill the holes in a bone 1 that are necessary to insert the locking screws in the distal locking holes 11;14. The dots 24 used to describe a geometric model of the distal locking holes 11;14 are automatically calculated based on the nail diameter D and the diameter d of the distal locking holes 11;14, i.e. these dots 24 are sampled from two continuous curves that are used to describe the intersections of two cylinders (one cylinder with the diameter D representing the distal end section 25 of the intramedullary nail 2 and the other cylinder with the diameter d representing a distal locking hole 11;14 each). This embodiment allows to apply the procedure as described above to a more complicated geometry of the distal end section 25 of an intramedullary nail 2, e.g. a conical distal end section 25 and/or distal locking holes 11;14 having different diameters d';d".

The invention claimed is:

1. A method for computer assisted localization of first and second distal locking holes in a distal end section of an implanted intramedullary nail having a nail axis and a nail tip, the method comprising the steps of:
   entering at least a nail diameter and a diameter of the first and second distal locking holes of the intramedullary nail in a data store of a computer;
   positioning an X-ray device with an optical axis with regard to the distal end section of the intramedullary nail irrespectively to the orientation of the distal locking holes whereby said optical axis is oriented essentially perpendicular to the nail axis;
   acquiring one single image of the distal end section of said intramedullary nail by means of the X-ray device;
   calculating the positions of the distal locking holes using the computer, the computer being programmed to automatically
      determine the position of the nail tip, the center of the first distal locking hole and the center of the second distal locking hole on the nail axis in the one single image,
      calculate a direction of the nail axis in a plane defined through the nail tip, at least one of the centers of the first and second distal locking holes, and a focal point of the X-ray device, and
      calculate the positions of the first and second hole axes of the first and second distal locking holes, respectively, with respect to a three-dimensional coordinate system defined by a dynamic reference base fixedly connected with the intramedullary nail or with a bone in which the intramedullary nail is implanted; and
   controlling a roboter provided with a drill bit having a drill axis using the computer whereby the drill axis of the drill bit is adjusted to align sequentially with each of the first and second hole axes of the first and second distal locking holes respectively as calculated in the calculating step and whereby the roboter guides the drill bit to drill separate holes in the bone for the insertion of locking screws in the first and second distal locking holes respectively.

2. The method of claim 1, wherein the single image of the distal end section of said intramedullary nail is taken by means of the X-ray device in a lateral-medial direction of said intramedullary nail implanted in a bone.

3. The method of claim 1, wherein the entering step includes entering a data set defining a geometrical model of said distal end section in the data store of the computer.

4. The method of claim 1, wherein the calculating the positions of the first and second hole axis of the first and second distal locking holes step is performed by an iterative closest projection point algorithm.

5. The method of claim 1, further comprising a step of measuring a position and orientation of the dynamic reference base with a position measurement device to establish a three-dimensional coordinate system fixedly connected with the intramedullary nail or with a bone in which the intramedullary nail is implanted.

6. A method for displaying a graphic representation of first and second distal locking holes in a distal end section of an implanted intramedullary nail having a nail axis and a nail tip, the method comprising:
   entering at least a nail diameter and a diameter of the first and second distal locking holes of the intramedullary nail in a data store of a computer;
   positioning an X-ray device with an optical axis with regard to the distal end section of the intramedullary nail irrespectively to the orientation of the distal locking holes such that said optical axis is oriented essentially perpendicular to the nail axis;
   acquiring one single image of the distal end section of said intramedullary nail by means of the X-ray device;
   calculating the positions of the distal locking holes by means of the computer which is programmed to automatically perform the steps of determining the position of the nail tip, the center of the first distal locking hole and the center of the second distal locking hole on the nail axis in the one single image, calculating a direction of the nail axis in a plane defined through the nail tip, at least one of the centers of the first and second distal locking holes, and a focal point of the X-ray device, and calculating the positions of the first and second hole axes of the first and second distal locking holes, respectively, with respect to a three-dimensional coordinate system defined by a dynamic reference base fixedly connected with the intramedullary nail or with a bone in which the intramedullary nail is implanted; and displaying the graphic representation of the first and second distal locking holes including trajectories of the axes of the first and second distal locking holes that define where a surgeon should accurately drill holes in a bone necessary to insert locking screws in the first and second distal locking holes.

7. The method of claim 1, wherein the X-ray device is a C-arm X-ray device.

8. The method of claim 1, wherein the X-ray device is a fluoroscope.

9. A device for the computer assisted drilling of holes in bone necessary for the insertion of locking screws in first and second distal locking holes in a distal end section of an implanted intramedullary nail having a nail axis, the device comprising:

a computer having a data store;

one or more first dynamic reference bases adapted to be connected with the intramedullary nail or with the bone in which the intramedullary nail is implanted;

a position measurement device for measuring the position and orientation of the one or more first dynamic reference bases;

an X-ray device with an optical axis, the X-ray device being provided with a second dynamic reference base; and a roboter provided with a drill bit having a drill axis for drilling holes for the distal locking of the implanted intramedullary nail;

wherein the computer is programmed to calculate the position of first and second hole axes of the first and second distal locking holes, respectively, with respect to the first and second dynamic reference bases using one single image of the distal end section of the intramedullary nail taken with the X-ray device whose optical axis is oriented essentially perpendicular to the nail axis but irrespective of the orientation of the distal locking holes by automatically performing the steps of determining the position of the nail tip, the center of the first distal locking hole and the center of the second distal locking hole on the nail axis in the one single image, calculating a direction of the nail axis in a plane defined through the nail tip, at least one of the centers of the first and second distal locking holes, and a focal point of the X-ray device, and calculating the positions of the first and second hole axes of the first and second distal locking holes, respectively, with respect to a three-dimensional coordinate system defined by a dynamic reference base fixedly connected with the intramedullary nail or with a bone in which the intramedullary nail is implanted, and wherein the computer is programmed to control the roboter to adjust the drill axis of the drill bit subsequently to each of the axes of the distal locking holes such that the roboter can guide the drill bit under control of the computer to drill the holes in the bone for the insertion of locking screws in the distal locking holes.

* * * * *